US008460620B2

(12) United States Patent
Bartfeld et al.

(10) Patent No.: US 8,460,620 B2
(45) Date of Patent: Jun. 11, 2013

(54) SPECIMEN COLLECTION CONTAINER ASSEMBLY

(75) Inventors: Benjamin R. Bartfeld, Ringwood, NJ (US); Robert G. Ellis, Wayne, NJ (US); Robert S. Golabek, Jr., Towaco, NJ (US); Nancy Dubrowny, Garfield, NJ (US); Girish Parmar, Easton, PA (US); Paul Holmes, New York, NY (US); Alex Blekher, Sussex, NJ (US); Michael Delk, Andover, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 13/295,235

(22) Filed: Nov. 14, 2011

(65) Prior Publication Data

US 2012/0141341 A1 Jun. 7, 2012

Related U.S. Application Data

(60) Provisional application No. 61/419,587, filed on Dec. 3, 2010.

(51) Int. Cl.

| | |
|---|---|
| ***B01L 3/14*** | (2006.01) |
| *B65D 25/00* | (2006.01) |
| *A61B 10/00* | (2006.01) |

(52) U.S. Cl.

USPC ........... 422/550; 220/737; 600/573; 422/547; 422/549

(58) Field of Classification Search

USPC ................. 422/215, 549–550, 558, 568–570, 422/913–914, 916; 73/864.63; 600/577

See application file for complete search history.

(56) References Cited

U.S. PATENT DOCUMENTS

| | | | | |
|---|---|---|---|---|
| 2,393,578 | A | | 1/1946 | Waite |
| 2,594,621 | A | | 4/1952 | Derrick |
| 2,698,272 | A | | 12/1954 | Clapp et al. |
| 2,998,726 | A | | 9/1961 | Peterson |
| 3,136,440 | A | * | 6/1964 | Krug et al. .................... 215/247 |
| 3,297,184 | A | | 1/1967 | Andelin |
| 3,430,798 | A | | 3/1969 | Goyet et al. |
| 3,552,591 | A | | 1/1971 | Wimmer |
| 3,630,191 | A | | 12/1971 | Gilford |

(Continued)

FOREIGN PATENT DOCUMENTS

| | | | |
|---|---|---|---|
| DE | 1187954 | | 2/1965 |
| DE | 19647673 | A1 | 5/1998 |
| EP | 0224650 | A2 | 6/1987 |
| EP | 0740155 | A1 | 10/1996 |
| WO | 2008031036 | A1 | 3/2008 |
| WO | 2009111622 | A2 | 9/2009 |

*Primary Examiner* — Jill Warden

*Assistant Examiner* — Julie Tavares

(74) *Attorney, Agent, or Firm* — The Webb Law Firm

(57) ABSTRACT

A specimen collection container includes inner and outer tubes. The inner tube includes a bottom end, a top end, and a sidewall extending therebetween defining an interior. The sidewall includes an inner surface and an outer surface having at least one annular protrusion extending therefrom. The inner tube includes at least one funnel portion adjacent the top end for directing a specimen into the inner tube interior, and an annular ring disposed about a portion of the outer surface of the sidewall adjacent the top end. The outer tube includes a bottom end, a top end, and a sidewall extending therebetween, the sidewall having an outer surface and an inner surface defining an annular recess adapted to receive a portion of the annular protrusion therein. The inner tube is disposed within the outer tube and a portion of the top end of the outer tube abuts the annular ring.

22 Claims, 16 Drawing Sheets

U.S. PATENT DOCUMENTS

| | | | | | |
|---|---|---|---|---|---|
| 3,760,969 | A | | 9/1973 | Shimamoto et al. | |
| 4,024,857 | A | | 5/1977 | Blecher et al. | |
| 4,092,113 | A | * | 5/1978 | Hardy | 436/177 |
| 4,156,570 | A | | 5/1979 | Wardlaw | |
| 4,163,500 | A | | 8/1979 | Gunne et al. | |
| 4,201,209 | A | | 5/1980 | LeVeen et al. | |
| 4,226,333 | A | | 10/1980 | Percarpio | |
| 4,227,620 | A | | 10/1980 | Conway | |
| 4,259,956 | A | | 4/1981 | Ogle | |
| 4,308,232 | A | | 12/1981 | Crouther et al. | |
| 4,381,275 | A | | 4/1983 | Sorensen | |
| 4,397,318 | A | | 8/1983 | Burns | |
| 4,411,163 | A | | 10/1983 | White | |
| 4,508,676 | A | | 4/1985 | Sorensen | |
| 4,512,486 | A | | 4/1985 | Kobayashi et al. | |
| 4,524,880 | A | | 6/1985 | Danielson et al. | |
| 4,558,947 | A | | 12/1985 | Wardlaw | |
| 4,576,185 | A | | 3/1986 | Proud et al. | |
| D285,115 | S | | 8/1986 | Proud et al. | |
| 4,620,549 | A | | 11/1986 | Nugent | |
| 4,635,807 | A | | 1/1987 | Knapp | |
| 4,682,703 | A | | 7/1987 | Kasai et al. | |
| 4,724,028 | A | | 2/1988 | Zabielski et al. | |
| 4,803,031 | A | | 2/1989 | Ochs et al. | |
| 4,805,635 | A | | 2/1989 | Korf et al. | |
| 4,869,384 | A | | 9/1989 | Ogle, II | |
| 4,893,636 | A | | 1/1990 | Cook et al. | |
| 4,967,919 | A | | 11/1990 | Earhart | |
| 4,982,614 | A | | 1/1991 | Gora | |
| 5,019,243 | A | | 5/1991 | McEwen et al. | |
| 5,038,794 | A | | 8/1991 | Van Valkenburg | |
| 5,060,812 | A | | 10/1991 | Ogle, II | |
| D321,456 | S | | 11/1991 | Wolff | |
| 5,078,941 | A | | 1/1992 | Tatsumi et al. | |
| D325,170 | S | | 4/1992 | Frantz | |
| 5,103,836 | A | * | 4/1992 | Goldstein et al. | 600/573 |
| D330,660 | S | | 11/1992 | Newton et al. | |
| D334,710 | S | | 4/1993 | Picozza | |
| 5,215,102 | A | | 6/1993 | Guirguis | |
| 5,217,668 | A | | 6/1993 | Matsuzaki et al. | |
| 5,232,109 | A | | 8/1993 | Tirrell et al. | |
| 5,277,874 | A | * | 1/1994 | Vasta | 422/560 |
| 5,279,606 | A | | 1/1994 | Haber et al. | |
| 5,286,453 | A | | 2/1994 | Pope | |
| 5,288,466 | A | | 2/1994 | Burns | |
| 5,379,907 | A | | 1/1995 | Niedospial et al. | |
| 5,384,096 | A | | 1/1995 | Burns | |
| 5,393,674 | A | | 2/1995 | Levine et al. | |
| D356,643 | S | | 3/1995 | Burns | |
| D357,985 | S | | 5/1995 | Burns | |
| 5,456,886 | A | | 10/1995 | Burns | |
| 5,458,113 | A | | 10/1995 | Burns | |
| 5,458,854 | A | | 10/1995 | Burns | |
| 5,484,566 | A | | 1/1996 | Gabbard | |
| 5,494,170 | A | | 2/1996 | Burns | |
| 5,522,518 | A | | 6/1996 | Konrad et al. | |
| 5,527,513 | A | | 6/1996 | Burns | |
| 5,552,117 | A | | 9/1996 | Burns | |
| 5,632,396 | A | | 5/1997 | Burns | |
| 5,651,998 | A | | 7/1997 | Bertschi et al. | |
| 5,672,321 | A | | 9/1997 | Daykin | |
| 5,699,923 | A | | 12/1997 | Burns | |
| 5,711,875 | A | | 1/1998 | Kayal et al. | |
| 5,714,125 | A | | 2/1998 | Sagstetter | |
| 5,716,683 | A | | 2/1998 | Harvey et al. | |
| 5,738,233 | A | | 4/1998 | Burns | |
| 5,779,074 | A | | 7/1998 | Burns | |
| 5,785,925 | A | | 7/1998 | U'Ren | |
| D397,295 | S | | 8/1998 | Shelton-Ferrell | |
| 5,789,033 | A | | 8/1998 | Bertschi et al. | |
| 5,798,069 | A | | 8/1998 | Bertschi et al. | |
| 5,888,184 | A | | 3/1999 | Wardlaw | |
| 5,889,581 | A | | 3/1999 | Tokuda | |
| 5,889,584 | A | | 3/1999 | Wardlaw | |
| 5,902,276 | A | | 5/1999 | Namey, Jr. | |
| 6,019,751 | A | | 2/2000 | Gabbard et al. | |
| 6,030,582 | A | | 2/2000 | Levy | |
| D425,625 | S | | 5/2000 | Niermann | |
| 6,056,925 | A | | 5/2000 | Sarstedt | |
| 6,071,454 | A | | 6/2000 | Shimizu et al. | |
| 6,074,612 | A | | 6/2000 | Sagstetter | |
| 6,077,235 | A | | 6/2000 | Serpentino et al. | |
| 6,080,366 | A | | 6/2000 | Kelly et al. | |
| 6,165,402 | A | | 12/2000 | Gabbard et al. | |
| 6,221,655 | B1 | | 4/2001 | Fung et al. | |
| 6,234,335 | B1 | | 5/2001 | Gee et al. | |
| D445,908 | S | | 7/2001 | Conway | |
| 6,322,739 | B1 | | 11/2001 | Andersson et al. | |
| 6,358,476 | B1 | | 3/2002 | Innamorato et al. | |
| 6,361,744 | B1 | | 3/2002 | Levy | |
| 6,426,049 | B1 | | 7/2002 | Rosen et al. | |
| 6,503,453 | B1 | | 1/2003 | Sagstetter | |
| D470,051 | S | | 2/2003 | Bloom et al. | |
| 6,524,295 | B2 | | 2/2003 | Daubert et al. | |
| 6,551,267 | B1 | | 4/2003 | Cohen et al. | |
| 6,562,300 | B2 | | 5/2003 | Rosen et al. | |
| 6,602,206 | B1 | | 8/2003 | Niermann et al. | |
| 6,607,685 | B2 | | 8/2003 | Naritomi et al. | |
| 6,610,041 | B2 | | 8/2003 | Daubert et al. | |
| D479,997 | S | | 9/2003 | Ekkert et al. | |
| 6,635,043 | B2 | | 10/2003 | Daubert et al. | |
| D481,801 | S | | 11/2003 | Whitley | |
| D481,946 | S | | 11/2003 | Nicholson et al. | |
| D481,948 | S | | 11/2003 | Brozell et al. | |
| 6,651,835 | B2 | | 11/2003 | Iskra | |
| 6,686,204 | B2 | | 2/2004 | Dubrowny et al. | |
| 6,716,396 | B1 | | 4/2004 | Anderson et al. | |
| 6,720,044 | B2 | | 4/2004 | Andersson et al. | |
| 6,727,101 | B1 | | 4/2004 | Sagstetter | |
| D489,610 | S | | 5/2004 | Miceli et al. | |
| D490,707 | S | | 6/2004 | Mataya | |
| 6,752,965 | B2 | | 6/2004 | Levy | |
| 6,806,094 | B2 | | 10/2004 | Anderson et al. | |
| 6,821,789 | B2 | | 11/2004 | Augello et al. | |
| 6,893,612 | B2 | | 5/2005 | Kacian et al. | |
| 6,910,597 | B2 | | 6/2005 | Iskra | |
| 6,939,514 | B1 | | 9/2005 | Mayes | |
| 7,022,289 | B1 | | 4/2006 | Schlein et al. | |
| 7,028,858 | B2 | | 4/2006 | Auer et al. | |
| 7,097,057 | B2 | | 8/2006 | Classens | |
| 7,137,519 | B2 | | 11/2006 | Becker | |
| 7,198,757 | B2 | | 4/2007 | Chiarin | |
| 7,210,593 | B2 | | 5/2007 | Stull et al. | |
| 7,276,383 | B2 | | 10/2007 | Iheme et al. | |
| 7,294,308 | B2 | | 11/2007 | Kacian et al. | |
| 7,309,468 | B2 | | 12/2007 | Stevens et al. | |
| 7,309,469 | B2 | | 12/2007 | Anderson et al. | |
| 7,334,310 | B2 | | 2/2008 | Becker | |
| D563,785 | S | | 3/2008 | Maki et al. | |
| 7,374,802 | B2 | | 5/2008 | Zihlmann | |
| 7,435,389 | B2 | | 10/2008 | Anderson et al. | |
| D607,340 | S | | 1/2010 | Klis | |
| 2001/0020607 | A1 | | 9/2001 | Chiarin | |
| 2002/0156439 | A1 | | 10/2002 | Iskra | |
| 2003/0028154 | A1 | | 2/2003 | Ross | |
| 2003/0039717 | A1 | | 2/2003 | Hwang et al. | |
| 2003/0133844 | A1 | | 7/2003 | Conway | |
| 2004/0006330 | A1 | | 1/2004 | Fangrow, Jr. | |
| 2004/0043505 | A1 | | 3/2004 | Walenciak et al. | |
| 2004/0045924 | A1 | | 3/2004 | Naritomi et al. | |
| 2004/0050846 | A1 | | 3/2004 | Iskra | |
| 2004/0118803 | A1 | | 6/2004 | Claessens | |
| 2004/0149287 | A1 | | 8/2004 | Namey, Jr. | |
| 2004/0223889 | A1 | * | 11/2004 | Reichenbach et al. | 422/102 |
| 2005/0059161 | A1 | | 3/2005 | Anderson et al. | |
| 2005/0090766 | A1 | | 4/2005 | Montanari | |
| 2006/0068206 | A1 | | 3/2006 | Hala et al. | |
| 2006/0089602 | A1 | | 4/2006 | Boucherie | |
| 2006/0175280 | A1 | | 8/2006 | Anraku et al. | |
| 2006/0200968 | A1 | | 9/2006 | Thilly et al. | |
| 2007/0173783 | A1 | | 7/2007 | Haindl | |
| 2007/0267776 | A1 | | 11/2007 | Conard et al. | |
| 2008/0047908 | A1 | | 2/2008 | Sekine et al. | |
| 2008/0072690 | A1 | | 3/2008 | Kacian et al. | |
| 2008/0110846 | A1 | | 5/2008 | Anderson et al. | |
| 2008/0125673 | A1 | * | 5/2008 | Carano et al. | 600/584 |
| 2008/0152545 | A1 | | 6/2008 | Anderson et al. | |

2008/0245163 A1 10/2008 Iheme et al.
2008/0274514 A1 11/2008 Dickey et al.
2008/0277370 A1 11/2008 Mikkelsen
2009/0308184 A1 12/2009 Blekher et al.

* cited by examiner

SPECIMEN COLLECTION CONTAINER ASSEMBLY

CROSS-REFERENCE TO RELATED APPLICATION

This application claims priority to U.S. Provisional Patent Application No. 61/419,587, filed Dec. 3, 2010, entitled “Specimen Collection Container Assembly”, the entire disclosure of which is herein incorporated by reference.

BACKGROUND OF THE INVENTION

1. Field of the Invention

The present invention relates to a specimen collection container assembly and, more particularly, to a specimen collection container assembly having improved sterility and suitable for use with automated clinical processes.

2. Description of Related Art

Medical capillary collection containers have historically been used for the collection of specimens, such as blood and other bodily fluids, for the purpose of performing diagnostic tests. Many of these capillary collection containers include a scoop or funnel for directing a specimen into the collection container. In most cases, capillary specimen collection containers are not sterile. In order to improve specimen quality, there is a desire for capillary collection devices to be sterile. In addition, there is a further desire to provide a capillary collection device in which the scoop or funnel is maintained in a sterile condition prior to use. Once a specimen is deposited within the specimen collection container, it is often desirable to maintain the specimen in a pristine condition prior to the performance of the intended diagnostic testing procedure.

In addition, clinical laboratory processes using specimen collection containers have become increasingly automated. As such, many conventional capillary specimen collection containers are not compatible with automated front end processes used to prepare a specimen for proper analysis, such as sorting specimen collection containers by type and/or contents, accessorizing specimen collection containers superficially or with additives specific to the contents of the specimen collection container, centrifugation, vision based specimen quality analysis, serum level analysis, decapping, aliquoting, and automated labeling of secondary tubes. In addition, many conventional capillary specimen collection containers are not compatible with automated analyzing procedures and are not dimensioned to accommodate automated diagnostic and/or analyzing probes or other specimen extraction equipment. Further, many conventional capillary specimen collection containers are not compatible with certain automated back end processes employed after a specimen is analyzed, such as resealing, storage, and retrieval.

SUMMARY OF THE INVENTION

Accordingly, a need exists for a capillary specimen collection container having improved sealing mechanisms for maintaining the sterility of the interior of the specimen collection container and/or the interior and exterior of the scoop or funnel. It is also desirable to maintain the purity of the specimen deposited within the specimen collection container prior to performance of a testing procedure.

In addition, a further need exists for a specimen collection container that is compatible with automated clinical laboratory processes, including front end automation, automated analyzers, and/or back end automation.

In accordance with an embodiment of the present invention, a specimen collection container includes an inner tube having a closed bottom end, a top end, and a sidewall extending therebetween defining an inner tube interior. The sidewall includes an inner surface and an outer surface having at least one annular protrusion extending therefrom. The inner tube also includes at least one funnel portion adjacent the top end for directing a specimen into the inner tube interior, and an annular ring disposed about a portion of the outer surface of the sidewall adjacent the top end. The specimen collection container also includes an outer tube including a bottom end, a top end, and a sidewall extending therebetween. The sidewall includes an outer surface and an inner surface defining an annular recess adapted to receive at least a portion of the annular protrusion therein. The inner tube is disposed at least partially within the outer tube and a portion of the top end of the outer tube abuts the annular ring.

In certain configurations, the inner tube and the outer tube are co-formed. The open top end of the inner tube may include a second funnel, such that the second funnel is substantially opposite the funnel. Optionally, at least one of the sidewall of the inner tube and the sidewall of the outer tube includes at least one fill-line. In other configurations, the closed bottom end of the outer tube includes at least one vent for venting air from the space defined between the inner surface of the outer tube and the outer surface of the inner tube. The outer surface of the inner tube may include at least one stabilizer extending therefrom for contacting a portion of the inner surface of the outer tube. In certain configurations, the inner tube completely seals the top end of the outer tube.

In further configurations, the specimen collection container may include a specimen collection cap sealing at least one of the top end of the inner tube and the top end of the outer tube. The specimen collection cap may include a top surface, an annular shoulder depending therefrom, and an annular interior wall depending from the top surface with the annular shoulder circumferentially disposed about the annular interior wall. A tube receiving portion may be defined between the annular shoulder and the annular interior wall, and at least a portion of the funnel may be received within the tube receiving portion.

In still further configurations, the annular shoulder may include an inner surface having a first protrusion extending therefrom into the tube receiving portion, and a second protrusion extending therefrom into the tube receiving portion, the first protrusion being laterally offset from the second protrusion. Additionally, a protrusion may be disposed on the outer surface of at least one of the inner tube and the outer tube, with the protrusion positioned between the first protrusion and the second protrusion of the annular shoulder when the specimen collection cap seals at least one of the top end of the inner tube and the top end of the outer tube. The inner surface of the annular shoulder may also include a third protrusion disposed about a bottom end of the specimen collection cap extending into the tube receiving portion for contacting a portion of the sidewall of at least one of the inner tube and the outer tube.

The specimen collection cap may also include an elastomeric stopper at least partially surrounded by the interior annular wall. The elastomeric stopper may be self-sealing. The elastomeric stopper may include a concave receiving surface adjacent the top surface of the specimen collection cap for directing an instrument to the apex of the concave receiving surface. Optionally, the elastomeric stopper may include an inverted receiving surface adjacent a bottom end of the specimen collection cap. The specimen collection cap may also include a plurality of ribs extending along a portion of an exterior surface of the annular shoulder.

In one configuration, the specimen collection cap includes a top surface and an annular shoulder depending therefrom having an inner surface, wherein at least a portion of the inner surface of the annular shoulder and the outer surface of the inner tube interact to form a seal. The seal may include a tortuous fluid path.

In another configuration, the specimen collection cap includes a top surface and an annular shoulder depending therefrom having an inner surface, wherein at least a portion of the inner surface of the annular shoulder and the outer surface of the outer tube interact to form a seal. The seal may include a tortuous fluid path.

DETAILED DESCRIPTION

Figure 1:
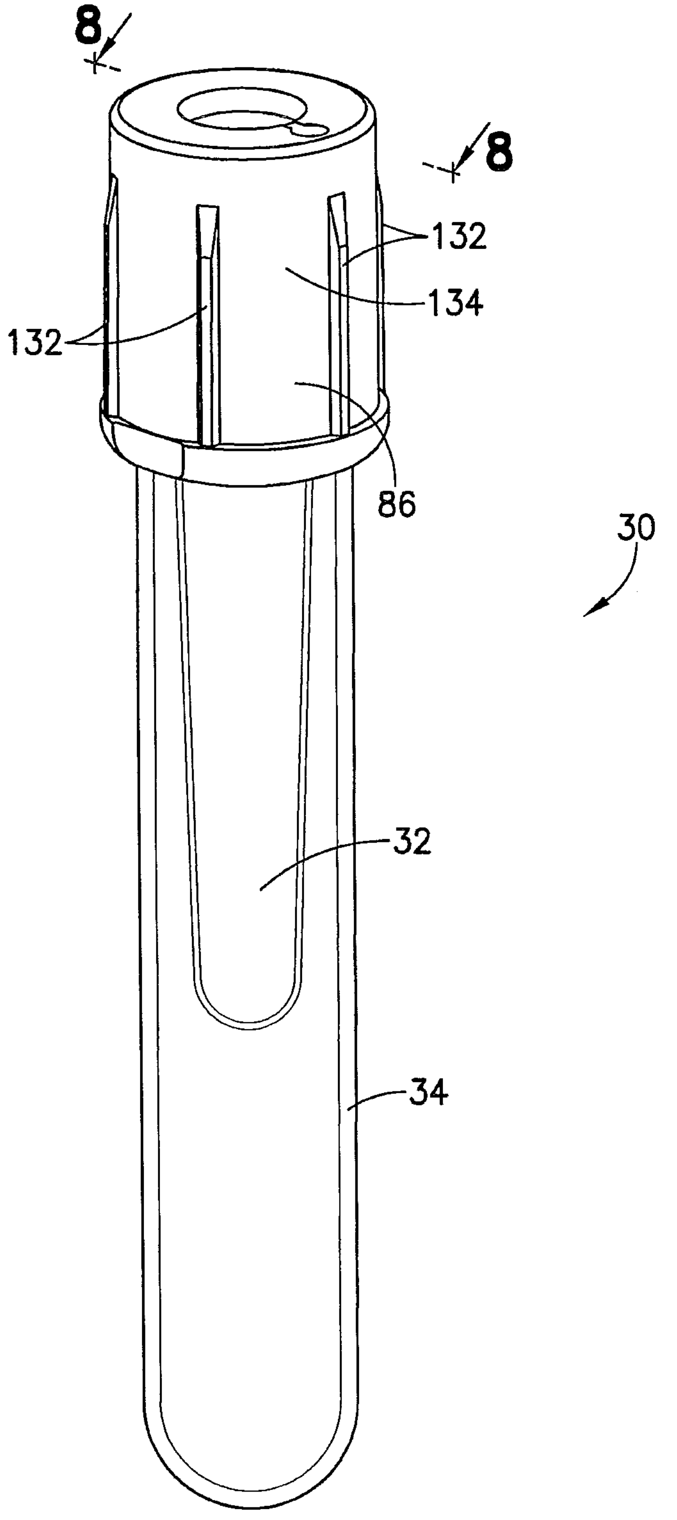
FIG. 1 is a frontwardly directed perspective view of a specimen collection container assembly in accordance with an embodiment of the present invention.
Figure 3:
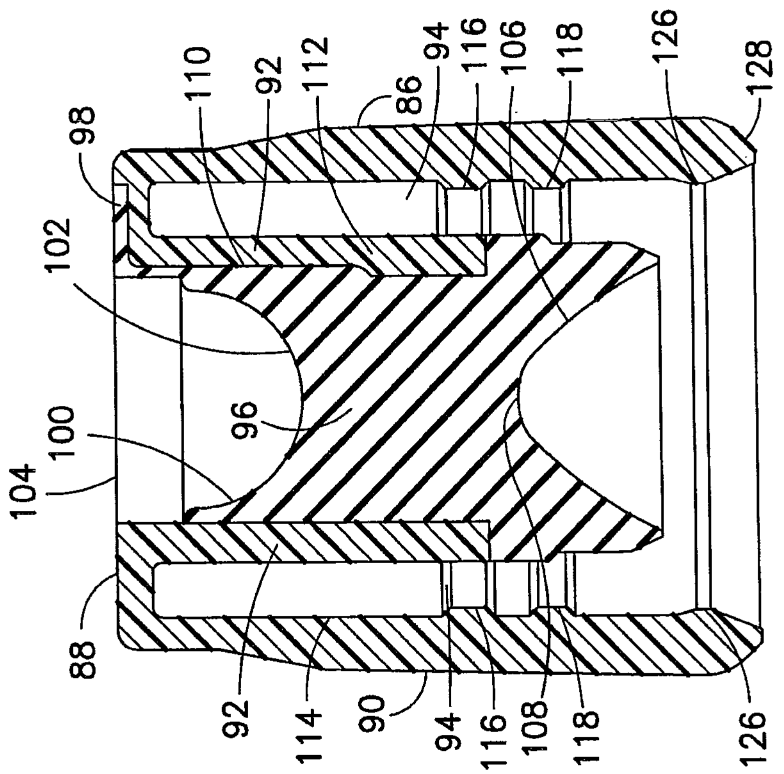
FIG. 3 is a cross-sectional view of the cap shown in FIG. 2 taken along line 3-3 in accordance with an embodiment of the present invention.
Figure 2:
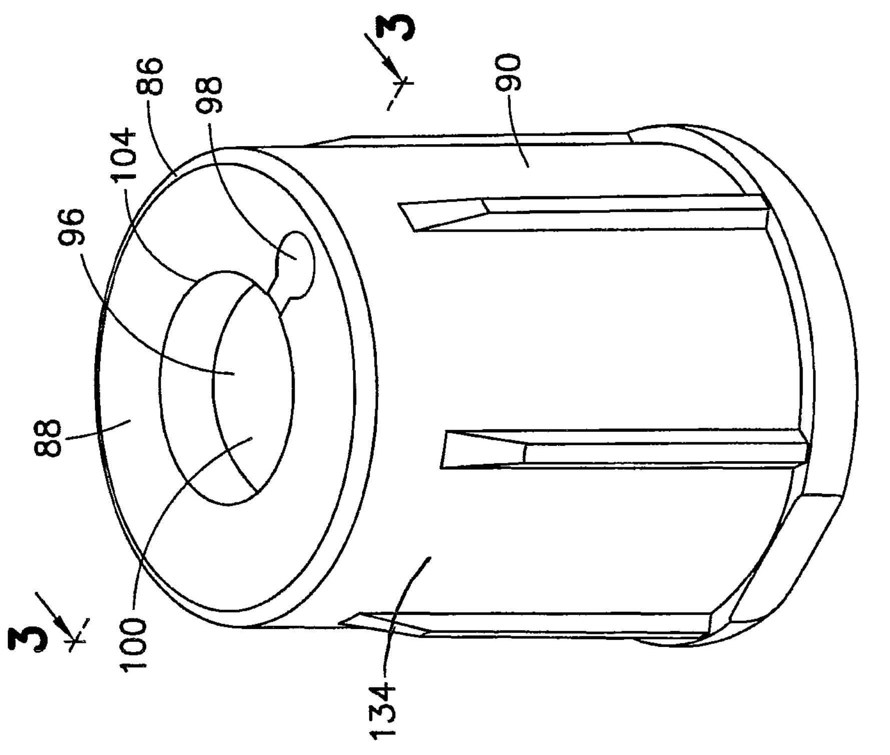
FIG. 2 is a perspective view of the cap of the specimen collection container assembly shown in FIG. 1 in accordance with an embodiment of the present invention.
Figure 4:
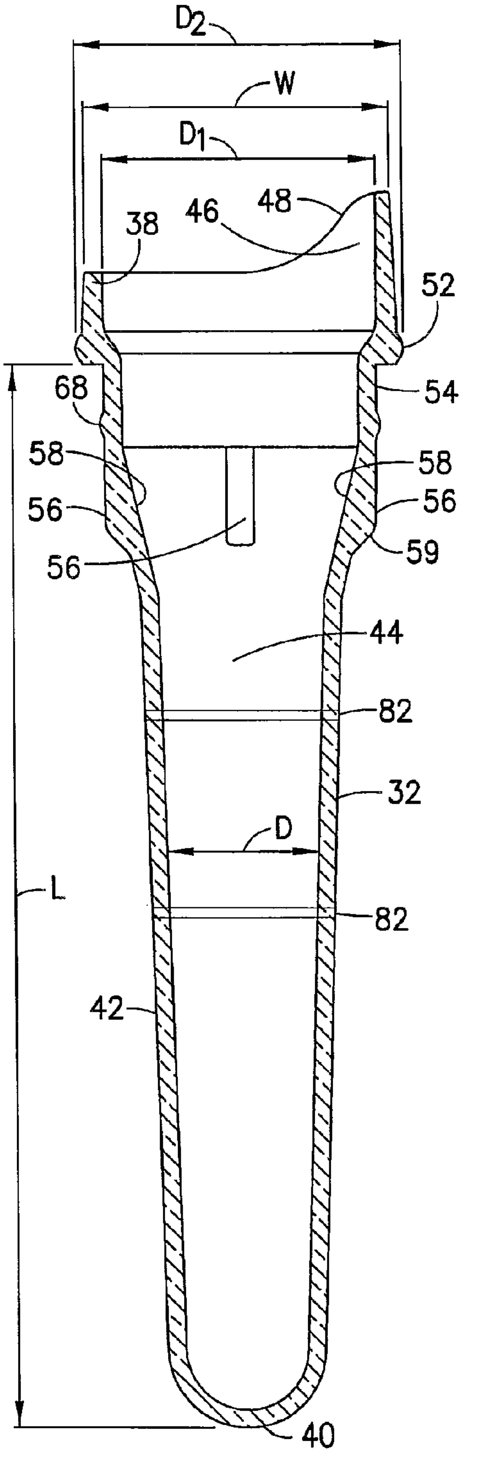
FIG. 4 is a front view of the inner tube having a funnel of the specimen collection container shown in FIG. 1 in accordance with an embodiment of the present invention.
Figure 5:
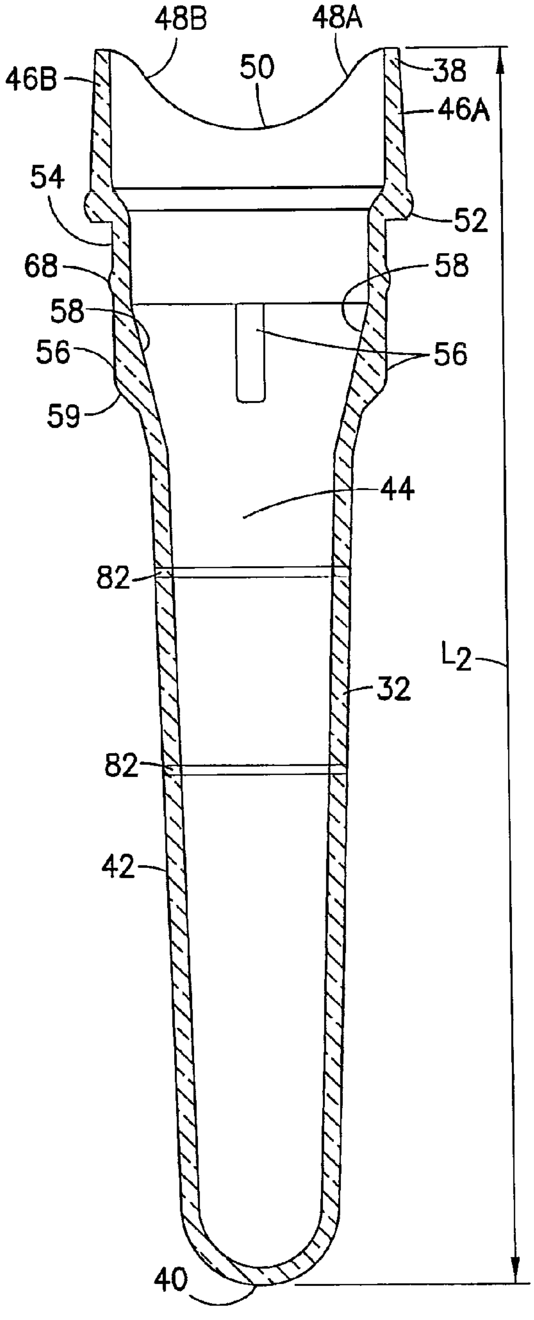
FIG. 5 is a front view of an alternative inner tube having dual funnels of the specimen collection container shown in FIG. 1 in accordance with an embodiment of the present invention.
Figure 6:
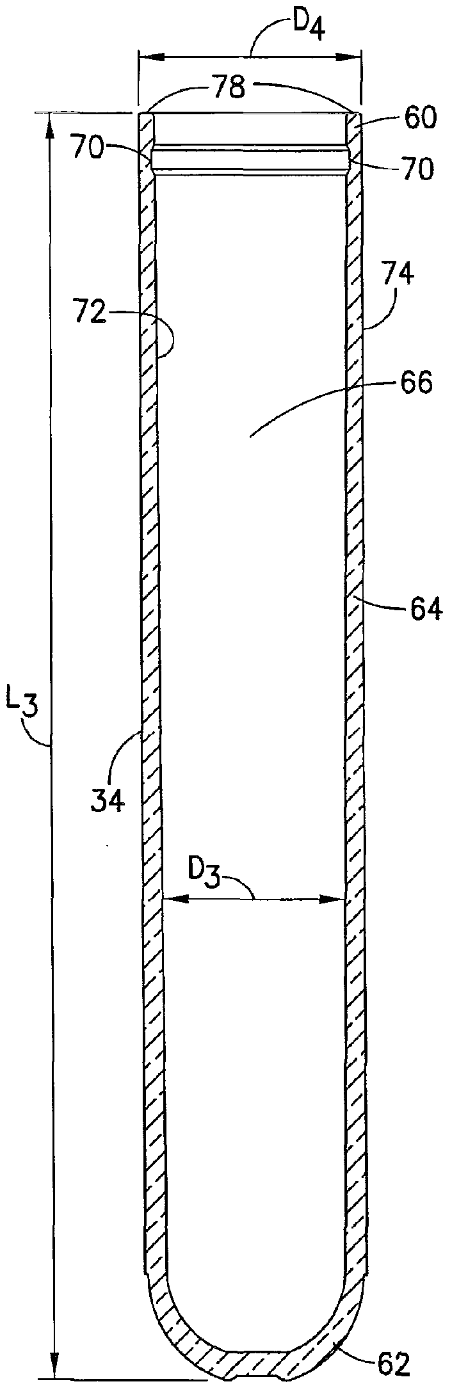
FIG. 6 is a front view of the outer tube of the specimen collection container shown in FIG. 1 in accordance with an embodiment of the present invention.
Figure 7:
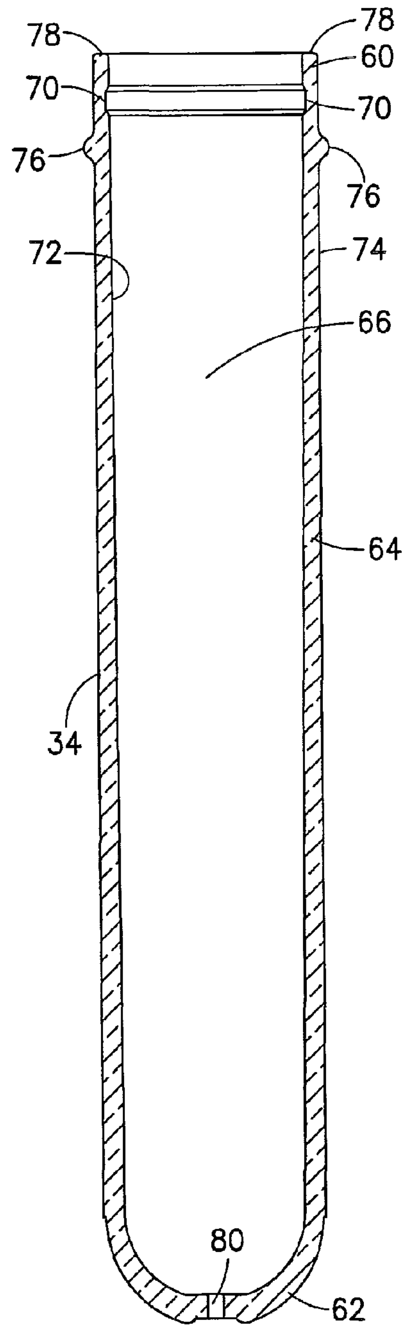
FIG. 7 is a front view of an alternative outer tube having an annular protrusion of the specimen collection container shown in FIG. 1 in accordance with an embodiment of the present invention.

As shown in FIG. 1, a specimen collection container assembly 30, such as a biological fluid collection container, includes an inner tube 32, an outer tube 34, and a specimen cap 86. The inner tube 32, as shown in FIGS. 4-5, is used for the collection and containment of a specimen, such as capillary blood or other bodily fluid, for subsequent testing procedures and diagnostic analysis. The outer tube 34, as shown in FIGS. 6-7, acts primarily as a carrier for the inner tube 32, providing additional protection for the contents of the inner tube 32 as well as providing external dimensions that are compatible with standard automated clinical laboratory processes, such as Clinical Laboratory Automation. The specimen cap 86, as shown in FIGS. 2-3, provides a means for a user to access the inner tube 32 to obtain the specimen deposited therein, and also provides a leak proof seal with the inner tube 32 upon replacement of the specimen cap 86, as will be discussed herein.

Referring specifically to FIGS. 4-5, the inner tube 32 includes an open top end 38, a closed bottom end 40, and a sidewall 42 extending therebetween defining an inner tube interior 44 adapted to receive a specimen therein. Referring to FIG. 4, the open top end 38 may include at least one funnel 46 or scoop portion for facilitating and directing a specimen into the interior 44 of the inner tube 32. The funnel 46 includes at least one introducing surface 48 having a curvature for guiding a specimen down the funnel 46 and into the interior 44 of the inner tube 32. In use, the funnel 46 may be placed adjacent a specimen and used to "scoop" the specimen into the inner tube 32. In certain instances the funnel 46 may be placed adjacent a patient's fingertip, and the funnel 46 may be used to scoop capillary blood into the inner tube 32.

Referring to FIG. 5, in other configurations, the open top end 38 of the inner tube 32 may include dual funnels 46A, 46B. The dual funnels 46A, 46B may be offset, such that the curvature of the introducing surface 48A of the first funnel 46A faces the corresponding curvature of the introducing surface 48B of the second funnel 46B, thereby forming a finger receiving surface 50. In use, a patient's finger tip may be placed in contact with the finger receiving surface 50 for directing capillary blood into the interior 44 of the inner tube 32.

The inner tube 32 may also include an annular ring 52 disposed about a portion of the sidewall 42. In certain configurations, the annular ring 52 is disposed adjacent the open top end 38 and extends outwardly from an exterior surface 54 of the sidewall 42. The inner tube 32 may further include an annular protrusion 68 extending outwardly from the exterior surface 54 of the sidewall 42. In another embodiment, the annular protrusion 68 may extend inwardly into an interior of the inner tube 32. In certain configurations, the annular protrusion 68 may be positioned below the annular ring 52.

The open top end 38 of the inner tube 32 may be adapted to provide a sufficiently wide opening to allow standard diagnostic and sampling probes, needles, and/or similar extraction or deposition devices to enter the open top end 38 and access the interior 44 for the purpose of depositing a specimen therein or withdrawing a specimen therefrom. In one embodiment, the interior 44 of the inner tube 32 may include at least one angled directing surface 58 for directing a standard instrument probe or other device toward the closed bottom end 40 of the inner tube 32. In certain configurations it is desirable for both the introducing surface 48 of the funnel 46 and the angled directing surface 58 to be smooth and gradual surfaces to promote the flow of specimen into the interior 44 of the inner tube 32.

In one embodiment, the dimensions of the inner tube 32 are balanced such that the open top end has an opening having a sufficient width W, as shown in FIG. 4, to allow a standard instrument probe to pass therethrough, and also to have an inner tube diameter D sufficient to provide the greatest column height of a specimen disposed within the interior 44 of the inner tube 32.

During a sampling procedure, an increased specimen column height within the inner tube 32, provides for a greater volume of specimen that may be retrieved or extracted by an analyzer probe (not shown).

At least one stabilizer 56 may be provided on the exterior surface 54 of the sidewall 42. The stabilizer 56, as shown in FIGS. 4-5, may have any suitable shape such that an outer surface 59 contacts at least a portion of the outer tube 34, as shown in FIGS. 6-7. Referring to FIGS. 6-7, the outer tube 34 has an open top end 60, a closed bottom end 62, and a sidewall 64 extending therebetween and forming an outer tube interior 66. The sidewall 64 of the outer tube 34 includes an inner surface 72 and an outer surface 74 and may include at least one recess 70 extending into a portion of the sidewall 64, such as into the inner surface 72 of a portion of the sidewall 64 adjacent the open top end 60. The recess 70 is adapted to receive at least a portion of the annular protrusion 68 of the inner tube 32 therein during assembly.

Referring to FIG. 7, the outer surface 74 may also include an annular ring 76 extending outwardly from the outer surface 74 of the sidewall 64 adjacent the open top end 60. In certain configurations, the annular ring 76 is positioned below the recess 70 along the sidewall 64.

Figure 8:
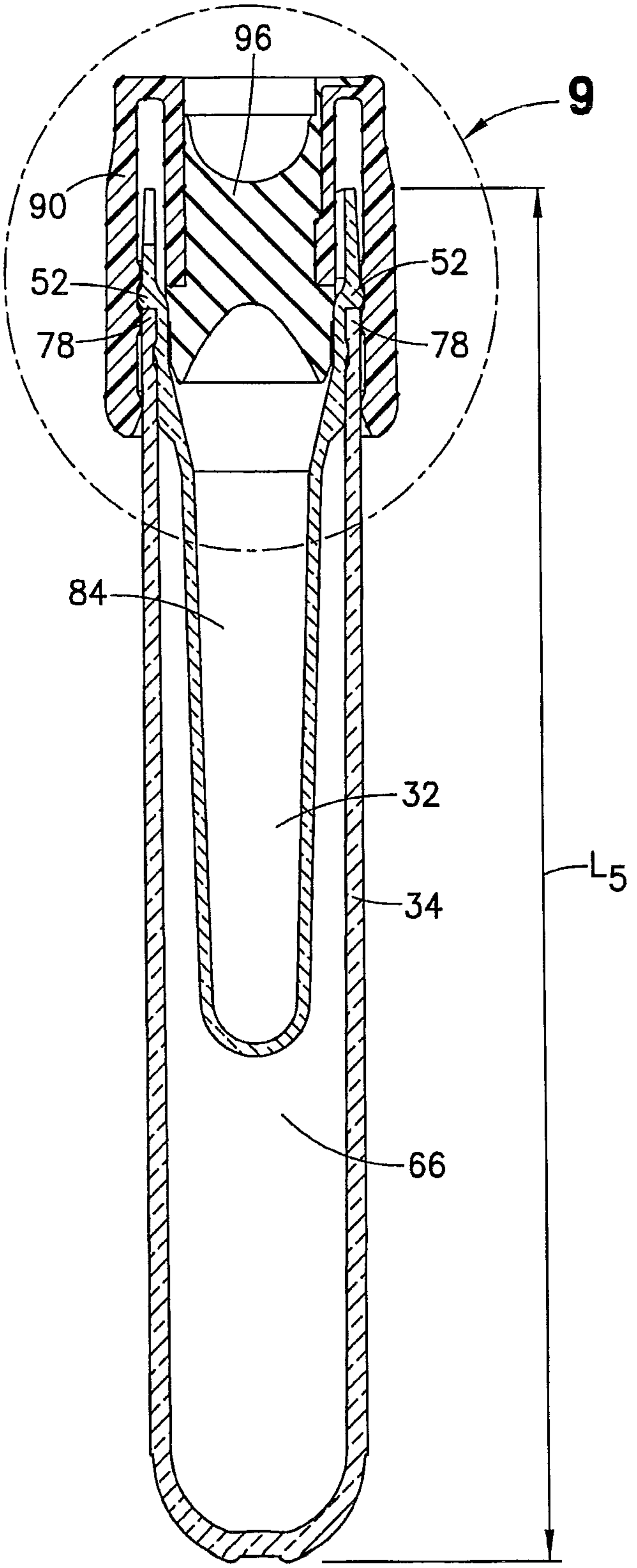
FIG. 8 is a cross-sectional side view of the specimen collection container assembly shown in FIG. 1 taken along line 8-8 in accordance with an embodiment of the present invention.
Figure 9:
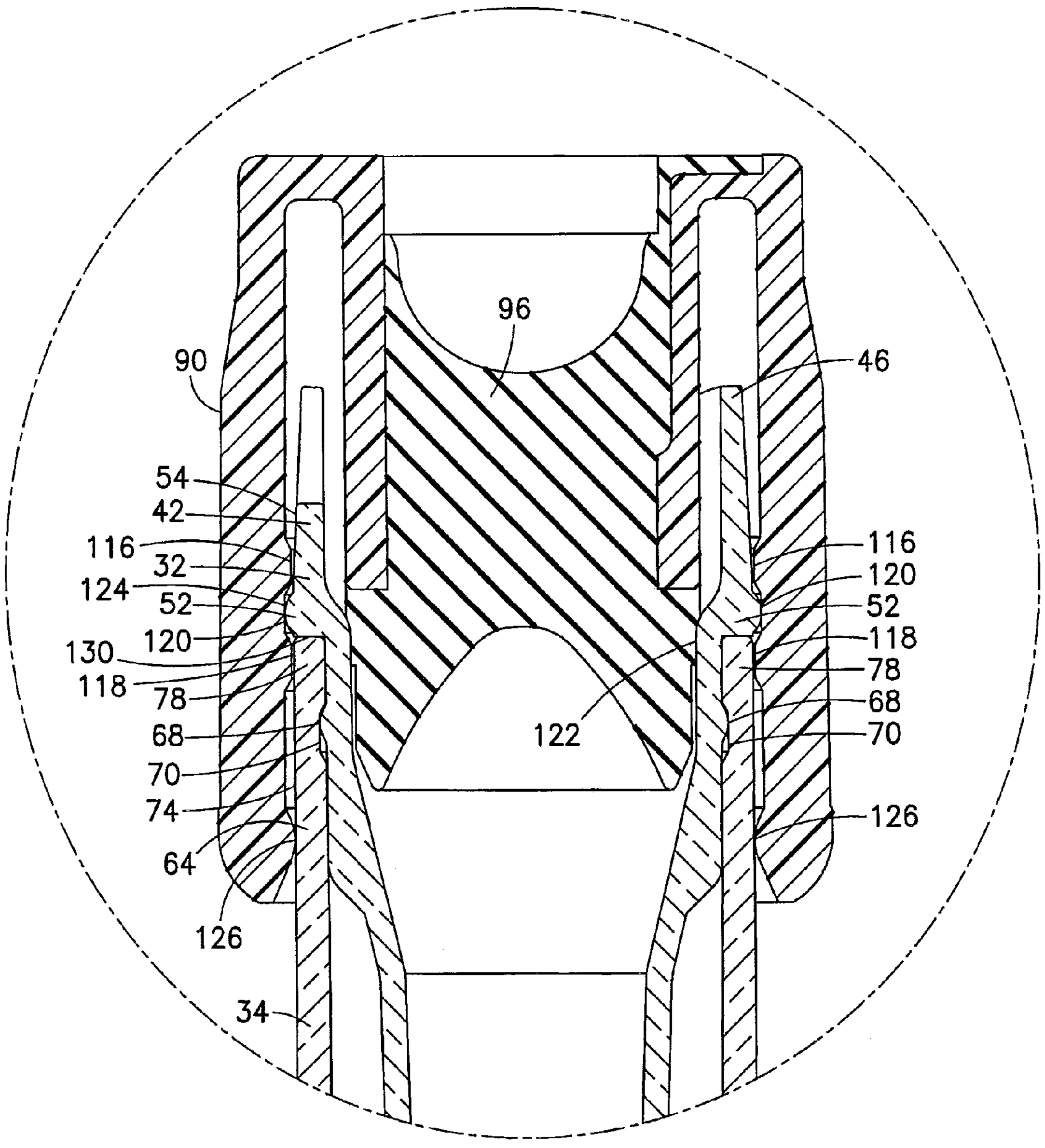
FIG. 9 is a close-up cross-sectional view of the cap shown in FIG. 8 taken along segment 9 in accordance with an embodiment of the present invention.
Figure 10:
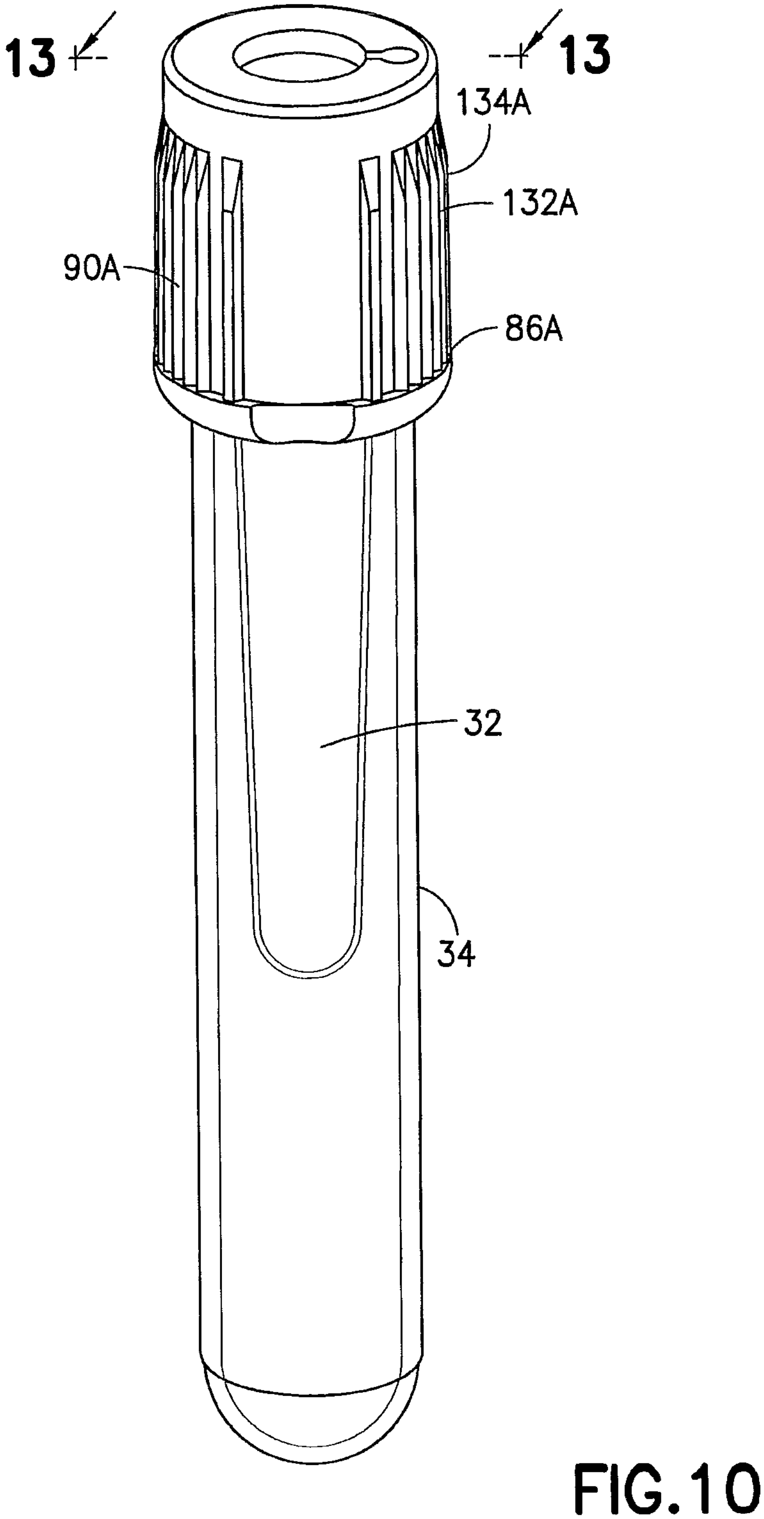
FIG. 10 is a frontwardly directed perspective view of an alternative embodiment of a specimen collection container assembly in accordance with an embodiment of the present invention.

Referring again to FIGS. 6-7, the outer tube 34 is dimensioned to receive the inner tube, as shown in FIGS. 4-5 at least partially therein, as shown in FIGS. 8-9. In one embodiment, the outer tube 34 has sufficient inner dimensions to accommodate the inner tube 32 therein. During assembly, the inner tube 32 may be at least partially positioned within the outer tube 34 such that an upper end 78 of the outer tube 34 abuts the annular ring 52 of the inner tube 32 allowing for a receiving portion of the inner tube having a length L, shown in FIG. 4, to be received within the outer tube interior 66, as shown in FIG. 8. Referring specifically to FIG. 4, the receiving portion of the inner tube 32 has a diameter $D_1$ that is dimensioned for receipt within the outer tube interior 66 and is smaller than the inner diameter $D_3$ of the outer tube 34, as shown in FIG. 6. The annular ring 52 of the inner tube 32 is dimensioned to restrain any further portion of the inner tube 32 from passing within the outer tube 34 and has a diameter $D_2$, shown in FIG. 4, that is greater than the inner diameter $D_3$ of the outer tube 34. As described above, during assembly the recess 70 of the outer tube 34 is adapted to receive at least a portion of the annular protrusion 68 of the inner tube 32 therein, as shown in FIGS. 8-9.

Although the inner tube 32 and the outer tube 34 may have any suitable dimensions, the inner tube may have an overall length $L_2$ of about 48 mm, as shown in FIG. 5, and have an inner tube diameter D of about 7 mm, as shown in FIG. 4. The outer tube 34 may have any suitable dimensions that are compatible with standard industry specifications for automated clinical processes, such as having an overall length $L_3$ of about 69 mm, as shown in FIG. 6, and an outer diameter $D_4$ of about 13 mm. The outer tube 34 may also be dimensioned to accommodate standard size labels applied to the outer surface 74 and may be dimensioned to improve manipulation by a clinician. This can be particularly advantageous when collecting small volume samples of specimen. A clinician can manipulate the outer tube 34, which is significantly easier to hold, while collecting a small volume specimen within the inner tube 32 disposed within the outer tube 34. When the inner tube 32 and the outer tube 34 are assembled, the overall length $L_5$ may be the industry standard length of 75 mm, as shown in FIG. 8, or an industry standard length of 100 mm.

In one embodiment, the inner tube 32 and the outer tube 34 may be in-molded in which both the inner tube 32 and the outer tube 34 are molded in the same press and assembled, as opposed to being separately molded and subsequently assembled. Alternatively, the inner tube 32 and the outer tube 34 may be press-fit within the same forming process. By forming both the inner tube 32 and the outer tube 34 together, the tolerances of the relative engagement between the inner tube 32 and the outer tube 34 may be improved because the relative rate of shrink is the same for both tubes. In certain configurations, the inner tube 32 and the outer tube 34 may be formed of the same material, such as polypropylene and/or polyethylene. In other configurations, the inner tube 32 and the outer tube 34 may be formed of two different polymeric materials. In certain embodiments it is noted that an assembly having an inner tube 32 and an outer tube 34 having thin walls allows for optical clarity of the sample when viewed by an automated vision system, assisting in sample and quality detection. In addition, increased optical clarity may assist a medical practitioner during collection of a specimen.

During assembly and/or formation of the inner tube 32 and the outer tube 34, air may become trapped between the inner surface 72 of the outer tube 34 and the exterior surface 54 of the sidewall 42 of the inner tube 32. Accordingly, the bottom end 62 of the outer tube 34 may include a vent 80, as shown in FIG. 7, for allowing air trapped between the inner surface of the outer tube 34 and the exterior surface 54 of the sidewall 42 of the inner tube 32 to escape therethrough. In certain configurations, the vent 80 may also assist in the molding process of the inner tube 32 by locking the core pin of the mold during the molding process to prevent relative shifting between the outer tube 34 and the formation of the inner tube 32.

In one embodiment of the present invention, at least one of the inner tube 32 and the outer tube 34 include at least one fill-line 82, shown in FIGS. 4-5, for allowing a clinician to determine the volume of specimen within the inner tube 32. In another embodiment, at least one of the inner tube 32 and the outer tube 34 includes a colored or light blocking additive 84, as shown in FIG. 8. The additive may allow sufficient light to pass through the sidewall 42 of the inner tube 32 to allow a clinician to visualize the contents of the interior 44 of the inner tube 32, and to also prevent enough light from passing through the sidewall 42 of the inner tube 32 to compromise or otherwise alter the contents of the inner tube 32. This application is particularly useful for specimens collected for light sensitive analytes, such as Bilirubin, as light degrades the specimen quality required for this testing procedure. In one embodiment, the additive may be sprayed, coated, or in-molded with at least one of the inner tube 32 and the outer tube 34. In another embodiment, the additive is intended to block only certain wavelengths of light from passing through the sidewall 42 of the inner tube 32.

Referring to FIGS. 2-3, a specimen collection cap 86 is provided for sealing the open top end 38 of the inner tube 32 and/or the open top end 60 of the outer tube 34. In one embodiment, once the inner tube 32 and the outer tube 34 are assembled, the open top end 60 of the outer tube 34 is sealed by the open top end 38 of the inner tube 32, specifically by the annular ring 52 of the inner tube 32. Accordingly, in this configuration the specimen collection cap 86 may only seal the open top end 38 of the inner tube 32 but effectively seals the open top end 60 of the outer tube 34 as well. The specimen collection cap 86 includes a top surface 88 and an annular shoulder 90 depending therefrom. The specimen collection cap 86 may also include an annular interior wall 92 depending from the top surface 88, with the annular shoulder 90 circumferentially disposed about the annular interior wall 92 and spaced therefrom by a tube receiving portion 94.

In one embodiment, an elastomeric stopper or pierceable septum 96 may be disposed at least partially within the annular interior wall 92 and extending therebetween forming a sealing body within the specimen collection cap 86. In one embodiment, the pierceable septum 96 is formed from a thermoplastic elastomer (TPE). The pierceable septum 96 may be pierced by a needle cannula or probe, as is conventionally known, and may be self-sealing. The pierceable septum 96 may be formed through an offset flow channel 98, as is described in United States Patent Publication No. 2009/0308184, the entire disclosure of which is hereby incorporated by reference. The pierceable septum 96 may include a concave receiving surface 100 adjacent the top surface 88 for directing an instrument, such as a needle cannula or a probe, to the apex 102 of the concave receiving surface 100. This allows a clinician to more easily determine proper placement of the needle cannula or probe for puncturing the pierceable septum 96. An opening 104 within the top surface 88 of the specimen collection cap 86 may also be dimensioned to accommodate standard clinical probes and needle cannulae for both hematology and chemistry analysis therethrough. The pierceable septum 96 also includes a specimen directing surface 106 for funneling a specimen into an apex 108 of the specimen collection cap 86 when the specimen collection container assembly 30, shown in FIG. 1, is inverted for specimen withdrawal, as is described in United States Patent Publication No. 2009/0308184.

Referring again to FIG. 3, the annular interior wall 92 may have an inner surface 110 contacting the pierceable septum 96. A portion of the inner surface 110 of the annular interior wall 92 may include a septum restraining portion 112 for preventing the inadvertent advancement of the pierceable septum 96 through the specimen collection cap 86 when pressure is applied to the pierceable septum 96 by a needle cannula or probe. The septum restraining portion 112 extends at least partially into the pierecable septum 96 for creating a physical restraint therebetween.

The annular shoulder 90 of the specimen collection cap 86 has an inner surface 114 having a first protrusion 116 extending from the inner surface 114 into the tube receiving portion 94, and a second protrusion 118 extending from the inner surface 114 into the tube receiving portion 94. The first protrusion 116 is spaced apart from the second protrusion 118, such as laterally offset therefrom along a portion of the inner surface 114 of the annular shoulder 90. The first protrusion 116 and the second protrusion 118 may extend annularly into the tube receiving portion 94.

As shown in FIGS. 8-9, when the specimen collection cap 86 and the inner tube 32 and outer tube 34 are combined, the annular shoulder 90 is positioned over the exterior surface 54 of the sidewall 42 of the inner tube 32 and the outer surface 74 of the sidewall 64 of the outer tube 34. The pierceable septum 96 contacts and forms a barrier seal 122 with a portion of the interior 44 of the inner tube 32, thereby sealing the interior 44 from the external atmosphere. The funnel 46, and portions of the open top end 38 of the inner tube 32 and the portions of the open top end 60 of the outer tube 34 are received within the tube receiving portion 94. The first protrusion 116 and the second protrusion 118 form a first recess 120 therebetween for accommodating the annular ring 52 of the inner tube 32 therein, thereby forming a first seal 124 between the specimen collection cap 86 and the inner tube 32.

Referring again to FIG. 3, the specimen collection cap 86 may also include a third protrusion 126 extending from the inner surface 114 of the annular shoulder 90 into the tube receiving portion 94. The third protrusion 126 may extend annularly into the tube receiving portion 94 and may be provided adjacent a bottom end 128 of the annular shoulder 90. Referring again to FIG. 9, when the specimen collection cap 86, inner tube 32, and outer tube 34 are combined, the third protrusion 126 may engage a portion of the outer surface 74 of the sidewall 64 of the outer tube 34 forming a second seal 130.

The barrier seal 122 formed between the pierceable septum 96 and the interior 44 of the inner tube 32 maintains the interior 44 in a sterile condition prior to receipt of a specimen therein. The barrier seal 122 also maintains the condition of the specimen present within the inner tube 32 after recapping or re-sealing of the pierceable septum 96. The first seal 124 and the second seal 130 form a tortuous path between the external atmosphere and the barrier seal 122 further enhancing the overall sealing system of the specimen collection container assembly 30, shown in FIG. 1. In addition, the first seal 124 and the second seal 130 maintain the funnel 46 in a sterile condition prior to use.

Optionally, as shown in FIGS. 1-2, the annular shoulder 90 of the specimen collection cap 86 may include a plurality of ribs 132 extending along a portion of an exterior surface 134 of the annular shoulder 90. These ribs 132 may be used to help identify the intended contents of the inner tube 32, additives and/or amounts of additives present within the inner tube 32, and/or the intended testing procedure to be performed on the contents of the inner tube 32.

With reference to FIGS. 10-14, an alternative specimen collection cap 86A is shown. The specimen collection cap 86A is adapted for use with the inner tube 32 and/or the outer tube 34 as described herein, and is substantially similar to the specimen collection cap 86, with several alternatives. Specifically, a sealing band 138 is disposed annularly about an interior surface 114A of an annular shoulder 90A and extends into a tube receiving portion 94A. The sealing band 138 forms a hermetic seal 136 with a portion of the outer surface 74 of the outer tube 34. In one embodiment, the sealing band 138 is deformable against an annular ring 76 extending from the outer surface 74 of the outer tube 34, as shown in FIG. 7, to form the hermetic seal 136. In certain embodiments, the annular shoulder 90A of the specimen collection cap 86A may include a strengthening member 140 adjacent the sealing band 138 for providing additional rigidity to the specimen collection cap 86A during engagement with the inner tube 32 and/or the outer tube 34.

The presence of the sealing band 138 at a bottom end 128A of the annular shoulder 90A allows for a reduction in the amount of material present in a pierceable septum 96A forming a barrier seal 122A with a portion of the interior 44 of the inner tube 32, thereby sealing the interior 44 from the external atmosphere. In this configuration, a seal 142 is formed by the interaction of the hermetic seal 136 and the interaction of a first protrusion 116A extending from the inner surface 114A of the annular shoulder 90A into the tube receiving portion 94A and the annular ring 52 of the inner tube 32. The seal 142 and the hermetic seal 136 form a tortuous path between the external atmosphere and the barrier seal 122A further enhancing the overall sealing system of the specimen collection container assembly 30, shown in FIG. 1.

In one embodiment, the engagement of the sealing band 138 and the annular ring 76 extending from the outer surface 74 of the outer tube 34 produces an audible and/or tactile indication that the specimen collection cap 86A and the outer tube 34 with the inner tube 32 disposed therein are sealingly engaged. In one configuration, the annular ring 76 may include a resistance protrusion and the sealing band 138 may include a corresponding resistance recess for accommodating the resistance protrusion therein.

Figure 12:
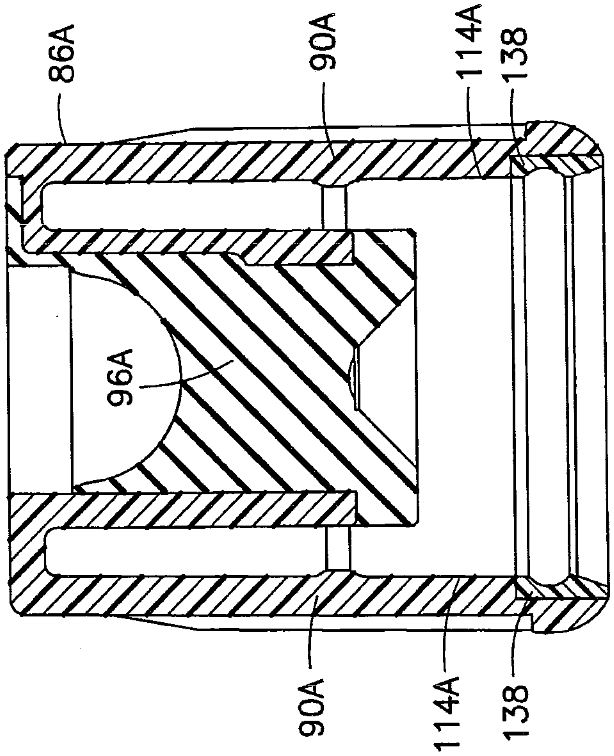
FIG. 12 is a cross-sectional view of the cap shown in FIG. 11 taken along line 12-12 in accordance with an embodiment of the present invention.
Figure 11:
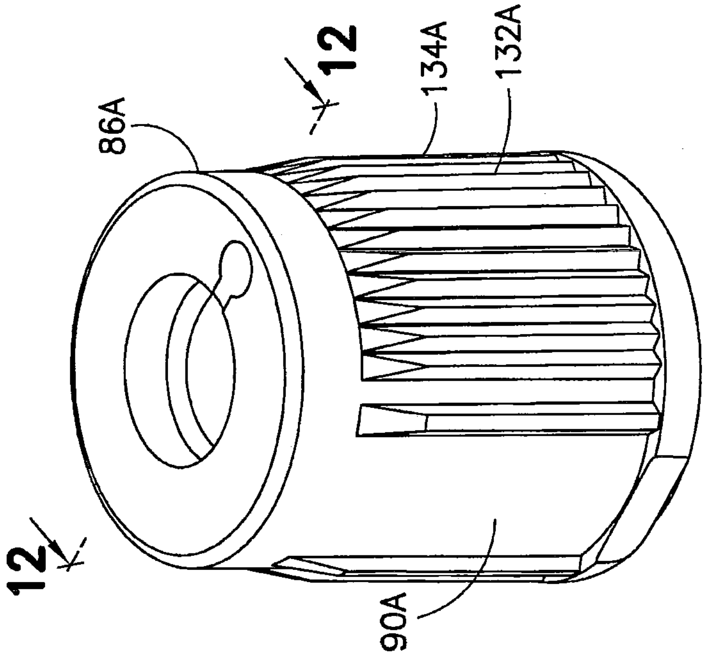
FIG. 11 is a perspective view of the cap of the specimen collection container assembly shown in FIG. 10 in accordance with an embodiment of the present invention.
Figure 13:
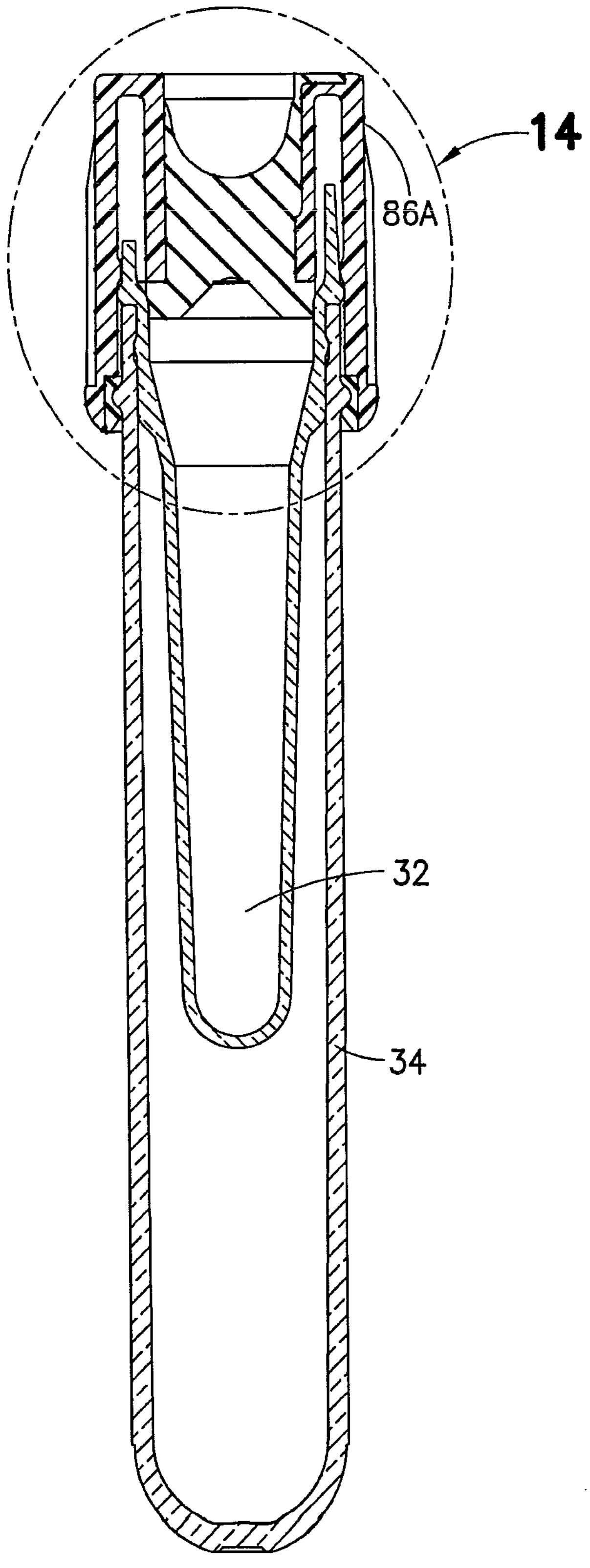
FIG. 13 is a cross-sectional side view of the specimen collection container assembly shown in FIG. 10 taken along line 13-13 in accordance with an embodiment of the present invention.
Figure 14:
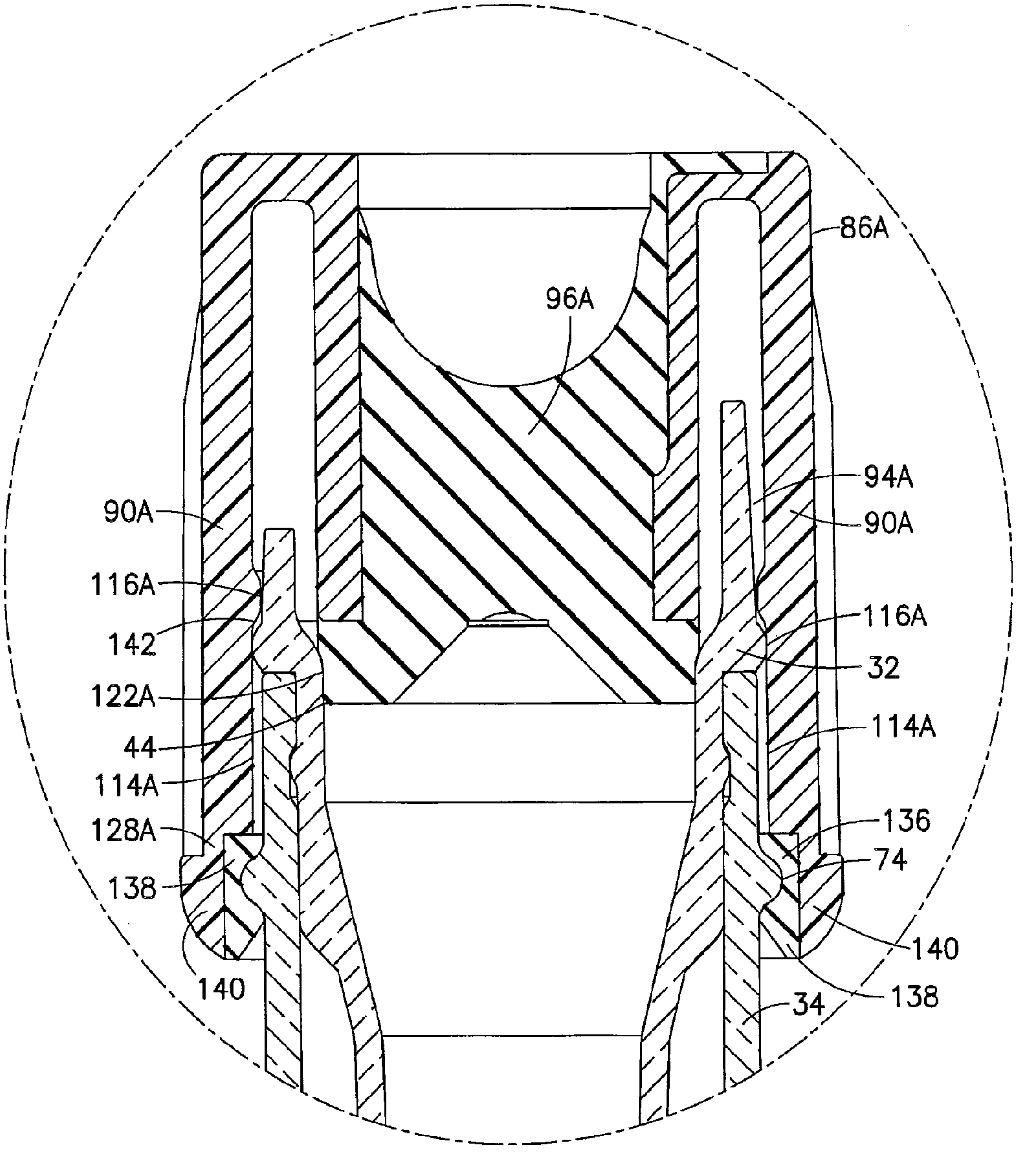
FIG. 14 is a close-up cross-sectional view of the cap shown in FIG. 13 taken along segment 14 in accordance with an embodiment of the present invention.

As shown in FIGS. 11-12, the annular shoulder 90A of the specimen collection cap 86A may include a plurality of alternative ribs 132A extending along a portion of an exterior surface 134A of the annular shoulder 90A. These ribs 132A may be used to help identify the intended contents of the inner tube 32, additives and/or amounts of additives present within the inner tube 32, and/or the intended testing procedure to be performed on the contents of the inner tube 32.

Figure 15:
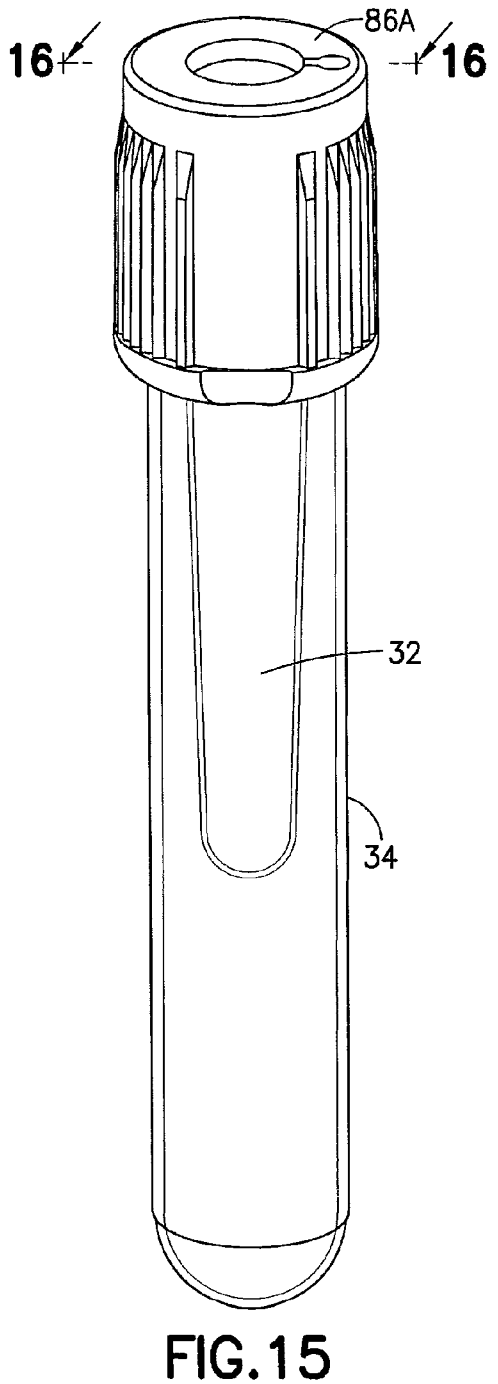
FIG. 15 is a frontwardly directed perspective view of an alternative embodiment of a specimen collection container assembly in accordance with an embodiment of the present invention.
Figure 16:
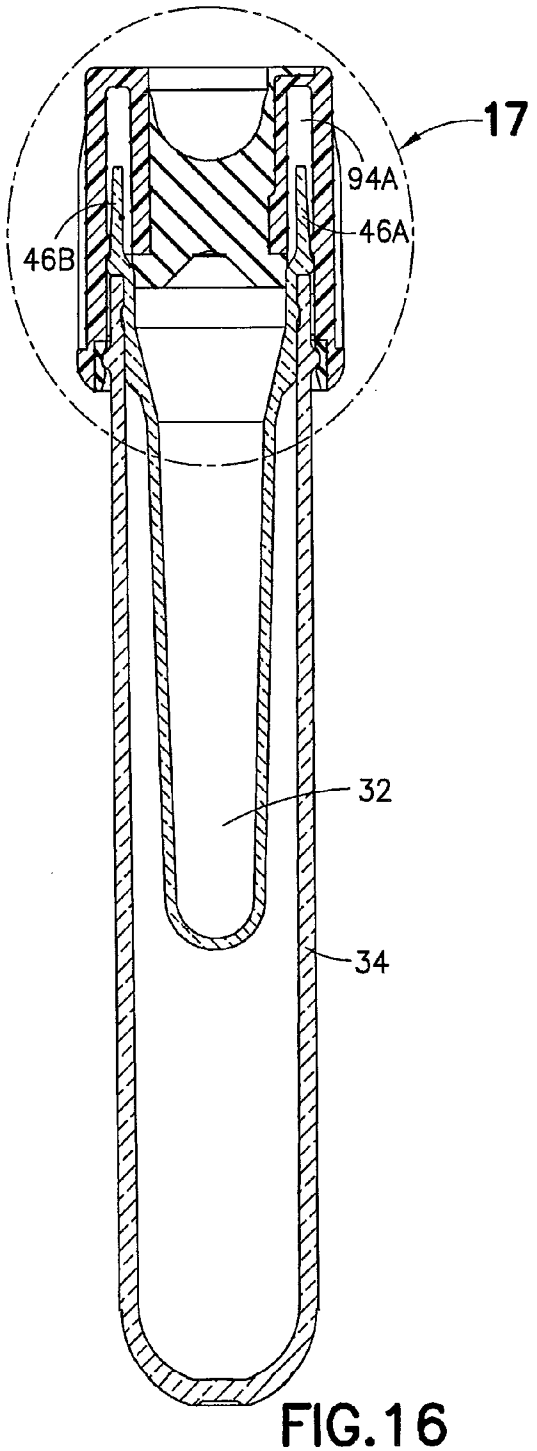
FIG. 16 is a cross-sectional side view of the specimen collection container assembly shown in FIG. 15 taken along line 16-16 in accordance with an embodiment of the present invention.
Figure 17:
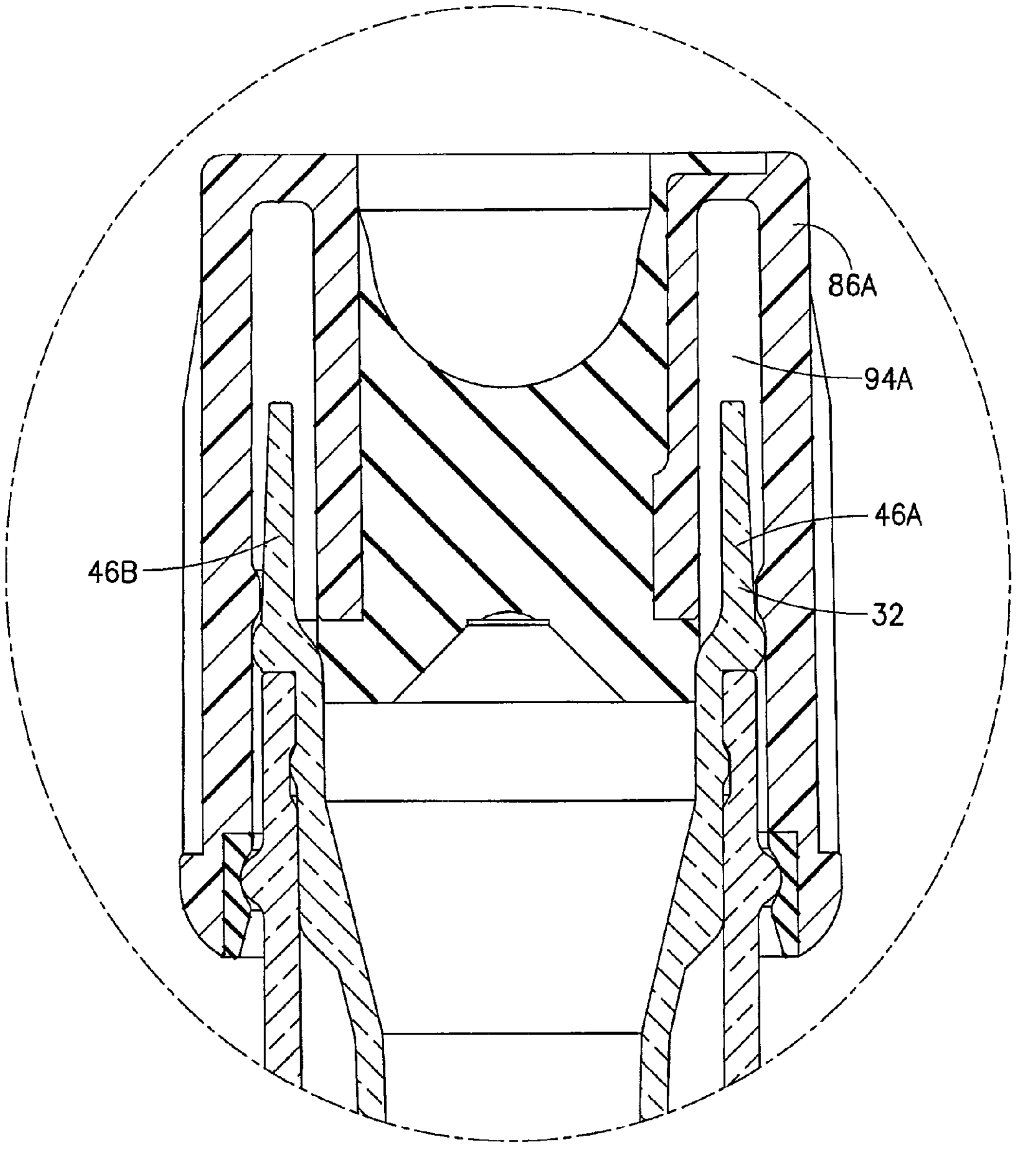
FIG. 17 is a close-up cross-sectional view of the cap shown in FIG. 16 taken along segment 17 in accordance with an embodiment of the present invention.

As shown in FIGS. 15-17, the specimen collection cap 86A is also suitable for use with inner tube 32 having dual funnels 46A, 46B. Referring specifically to FIG. 17, the dual funnels 46A, 46B are each received within the tube receiving portion 94A, as described herein.

Referring to FIGS. 18-22, an alternative specimen collection cap 86B is shown. The specimen collection cap 86B is adapted for use with the inner tube 32 and/or the outer tube 34 as described herein, and is substantially similar to the specimen collection cap 86, with several alternatives. Specifically, in accordance with an embodiment of the present invention, the specimen collection cap 86B includes a top surface 88B having an annular shoulder 90B depending therefrom and at least partially surrounding the pierceable septum 96B. In this configuration, the pierceable septum 96B includes a base portion 144 and an outer portion 146 circumferentially disposed about the base portion 144 and defining a tube receiving portion 148 therebetween.

When the specimen collection cap 86B and the inner tube 32 and outer tube 34 are assembled, the funnel 46, such as dual funnels 46A, 46B, is received within the tube receiving portion 148. The tube receiving portion 148 may be dimensioned such that a spacing gap 152 is present on either side of the funnels 46A, 46B when the inner tube 32 is engaged with the specimen collection cap 86B. The spacing gap 152 reduces contact between the funnels 46A, 46B and the pierceable septum 96B during assembly of the specimen collection cap 86B and the inner tube 32. This may be particularly advantageous for preventing or minimizing pull-away of the pierceable septum 96B during disengagement of the specimen collection cap 86B and the inner tube 32.

In a further embodiment, a bottom end 150 of the outer portion 146 of the pierceable septum 96B may include a tapered surface 154 for guiding the open top end 38, particularly the funnels 46A, 46B into the tube receiving portion 148 of the pierceable septum 96B.

The pierceable septum 96B may contact and form a barrier seal 122 with a portion of the interior 44 of the inner tube 32, thereby sealing the interior 44 from the external atmosphere, as described herein. The pierceable septum 96B may also form a perimeter seal 156 between a portion of the outer portion 146 and the annular ring 52 of the inner tube 32. In certain configurations, an upper tip 160 of the funnels 46A, 46B may contact an uppermost region 162 of the tube receiving portion 148 forming a tertiary seal 164 therebetween. The tertiary seal 164 and the perimeter seal 156 form a tortuous path between the external atmosphere and the barrier seal 122 further enhancing the overall sealing system of a specimen collection container assembly 30B, shown in FIG. 18.

In a further embodiment, an inner surface 114B of the annular shoulder 90B may include a septum restraining portion 112B for preventing the inadvertent advancement of the pierceable septum 96B through the specimen collection cap 86B when pressure is applied to the pierceable septum 96B by a needle cannula or probe. The septum restraining portion 112B extends at least partially into the pierceable septum 96B for creating a physical restraint therebetween. In still a further embodiment, the pierceable septum 96B may include a restraining portion 170 for bearing against an inner surface 172 of the top surface 88B for preventing inadvertent disengagement of the specimen collection cap 86B.

Figure 18:
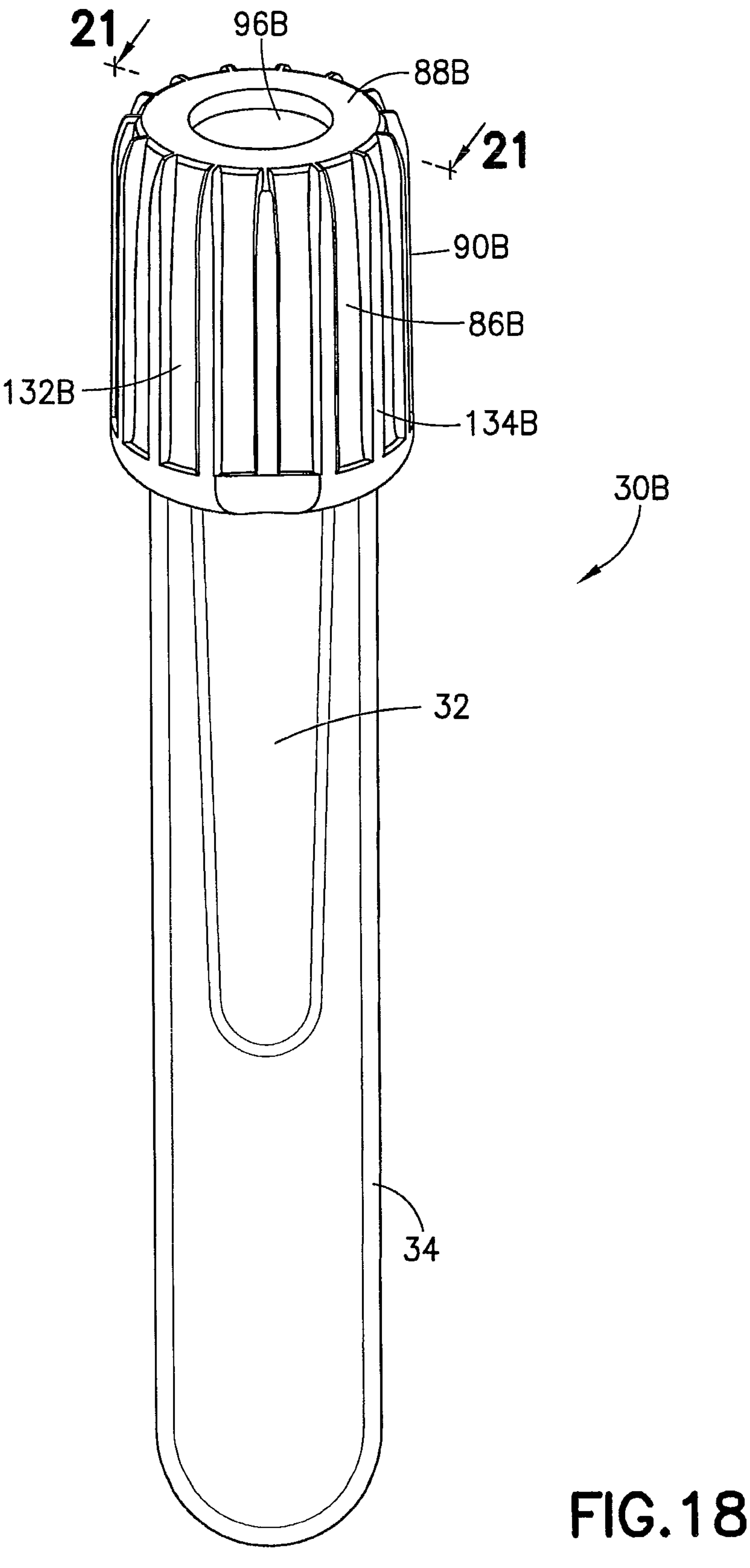
FIG. 18 is a frontwardly directed perspective view of an alternative embodiment of a specimen collection container assembly in accordance with an embodiment of the present invention.
Figure 20:
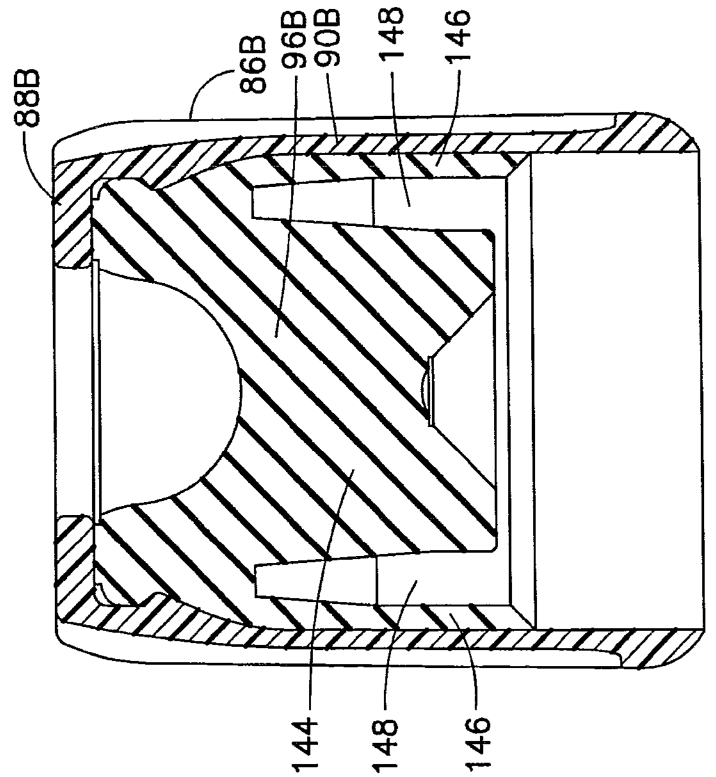
FIG. 20 is a cross-sectional view of the cap shown in FIG. 19 taken along line 20-20 in accordance with an embodiment of the present invention.
Figure 19:
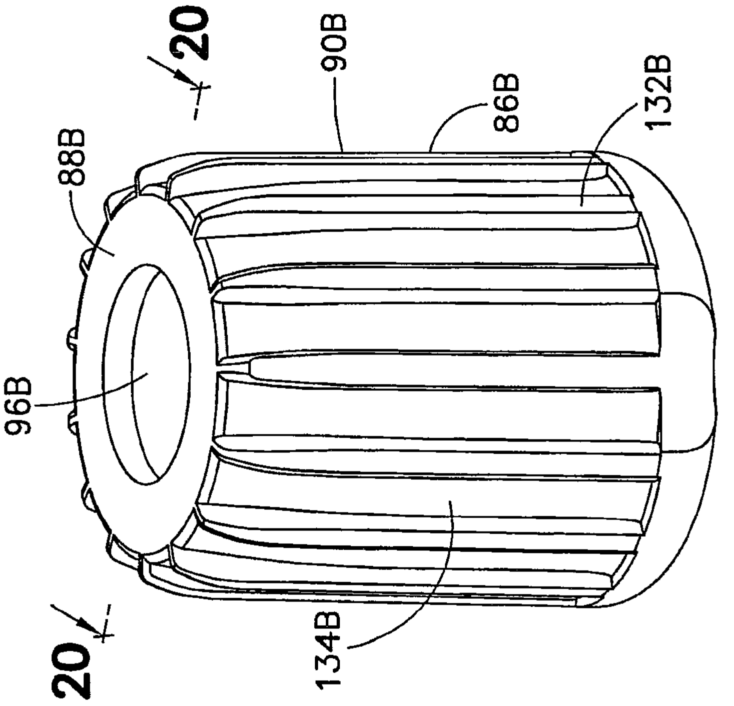
FIG. 19 is a perspective view of the cap of the specimen collection container assembly shown in FIG. 18 in accordance with an embodiment of the present invention.
Figure 21:
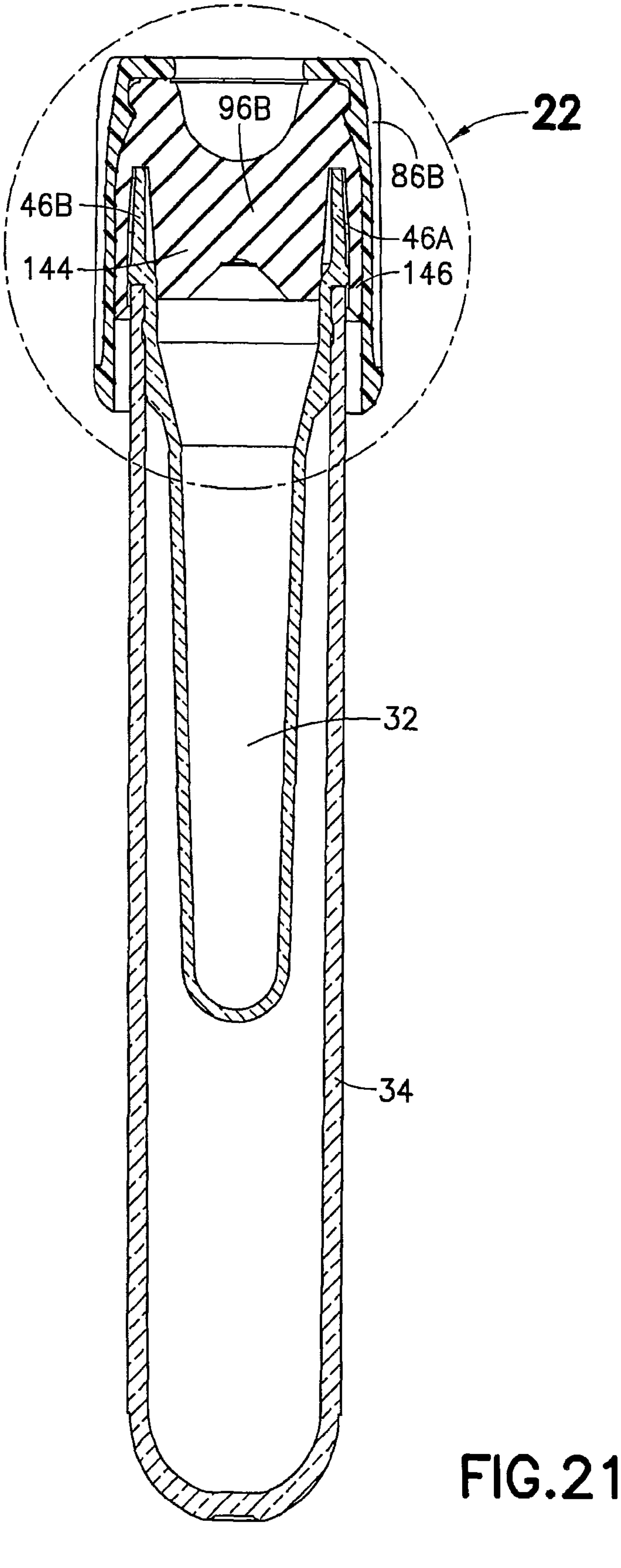
FIG. 21 is a cross-sectional side view of the specimen collection container assembly shown in FIG. 18 taken along line 21-21 in accordance with an embodiment of the present invention.
Figure 22:
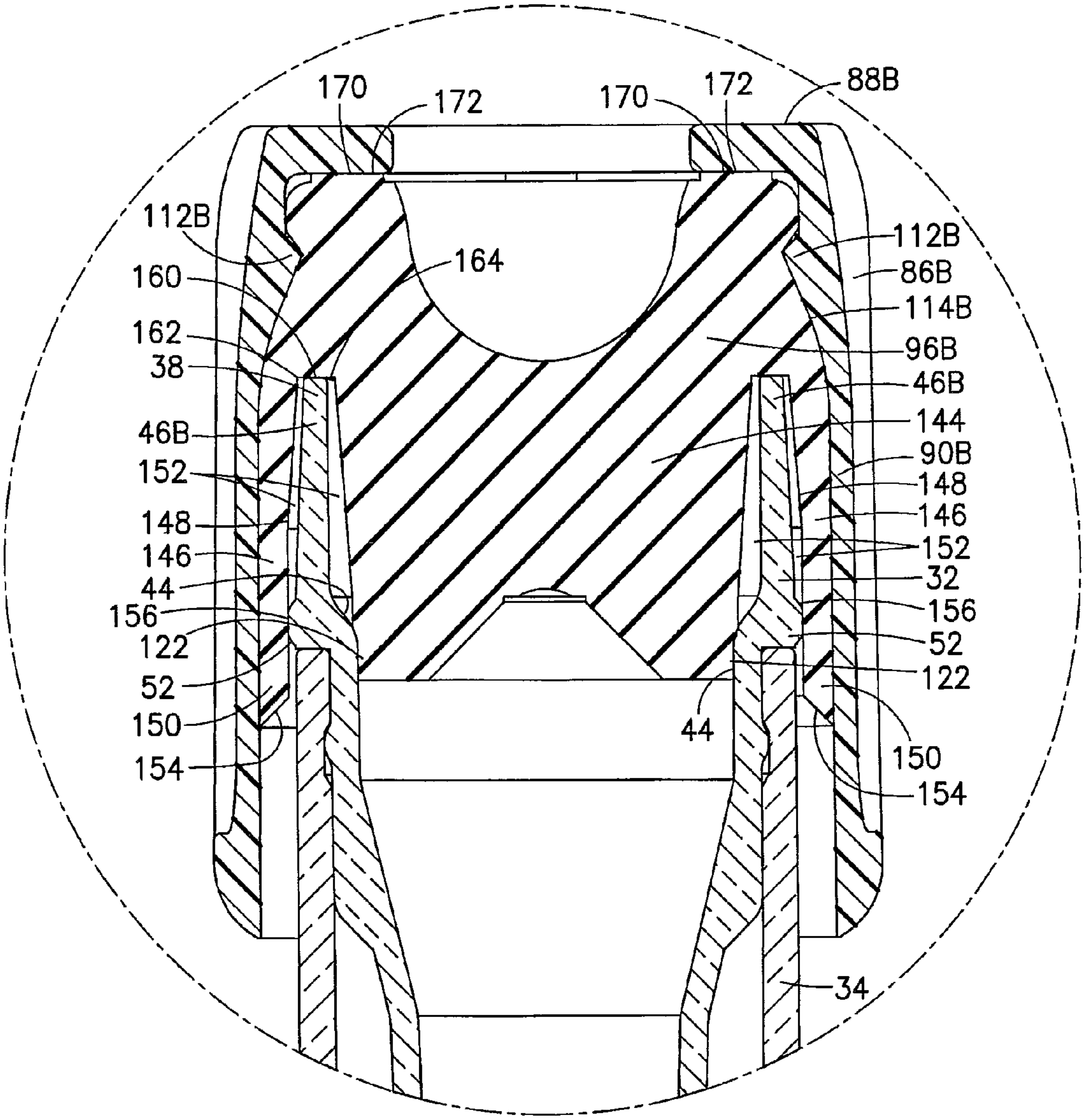
FIG. 22 is a close-up cross-sectional view of the cap shown in FIG. 21 taken along segment 22 in accordance with an embodiment of the present invention.

As shown in FIGS. 18-19, the annular shoulder 90B of the specimen collection cap 86B may include a plurality of alternative ribs 132B extending along a portion of an exterior surface 134B of the annular shoulder 90B. These ribs 132B may be used to help identify the intended contents of the inner tube 32, additives and/or amounts of additives present within the inner tube 32, and/or the intended testing procedure to be performed on the contents of the inner tube 32.

While specific embodiments of the invention have been described in detail, it will be appreciated by those skilled in the art that various modifications and alternatives to those details could be developed in light of the overall teachings of the disclosure.

What is claimed is:

1. A specimen collection container, comprising:

an inner tube having a closed bottom end, a top end, and a sidewall extending therebetween defining an inner tube interior, the sidewall having an inner surface and an outer surface having at least one annular protrusion extending therefrom, the inner tube comprising at least one funnel portion adjacent the top end for directing a specimen into the inner tube interior, and an annular ring disposed about a portion of the outer surface of the sidewall adjacent the top end, the funnel portion being adjacent to and above the annular ring; and an outer tube comprising a bottom end, a top end including a upper end , and a sidewall extending therebetween, the sidewall having an outer surface and an inner surface defining an annular recess adapted to receive at least a portion of the annular protrusion therein, wherein the inner tube is disposed at least partially within the outer tube such that the funnel portion sits above the upper end and a portion of the upper end of the outer tube abuts the annular ring.

2. The specimen collection container of claim 1, wherein the inner tube and the outer tube are co-formed.

3. The specimen collection container of claim 1, wherein the open top end of the inner tube comprises a second funnel, such that the second funnel is substantially opposite the funnel.

4. The specimen collection container of claim 1, wherein at least one of the sidewall of the inner tube and the sidewall of the outer tube includes at least one fill-line.

5. The specimen collection container of claim 1, wherein the bottom end of the outer tube comprises at least one vent for venting air from the space defined between the inner surface of the outer tube and the outer surface of the inner tube.

6. The specimen collection container of claim 1, wherein the outer surface of the inner tube comprises at least one stabilizer extending therefrom for contacting a portion of the inner surface of the outer tube.

7. The specimen collection container of claim 1, wherein the inner tube completely seals the top end of the outer tube.

8. The specimen collection container of claim 1, further comprising a specimen collection cap sealing at least one of the top end of the inner tube and the top end of the outer tube.

9. The specimen collection container of claim 8, wherein the specimen collection cap includes a top surface, an annular shoulder depending therefrom, and an annular interior wall depending from the top surface with the annular shoulder circumferentially disposed about the annular interior wall.

10. The specimen collection container of claim 9, wherein a tube receiving portion is defined between the annular shoulder and the annular interior wall, and wherein at least a portion of the funnel is received within the tube receiving portion.

11. The specimen collection container of claim 10, wherein the annular shoulder comprises an inner surface having a first protrusion extending therefrom into the tube receiving portion, and a second protrusion extending therefrom into the tube receiving portion, the first protrusion laterally offset from the second protrusion.

12. The specimen collection container of claim 11, further comprising a protrusion disposed on the outer surface of at least one of the inner tube and the outer tube, the protrusion positioned between the first protrusion and the second protrusion of the annular shoulder when the specimen collection cap seals at least one of the top end of the inner tube and the top end of the outer tube.

13. The specimen collection container of claim 10, wherein the inner surface of the annular shoulder further comprises a third protrusion disposed about a bottom end of the specimen collection cap extending into the tube receiving portion for contacting a portion of the sidewall of at least one of the inner tube and the outer tube.

14. The specimen collection container of claim 9, further comprising an elastomeric stopper at least partially surrounded by the interior annular wall.

15. The specimen collection container of claim 14, wherein the elastomeric stopper is self-sealing.

16. The specimen collection container of claim 14, wherein the elastomeric stopper comprises a concave receiving surface adjacent the top surface of the specimen collection cap for directing an instrument to an apex of the concave receiving surface.

17. The specimen collection container of claim 14, wherein the elastomeric stopper comprises an inverted receiving surface adjacent a bottom end of the specimen collection cap.

18. The specimen collection container of claim 9, further comprising a plurality of ribs extending along a portion of an exterior surface of the annular shoulder.

19. The specimen collection container of claim 8, wherein the specimen collection cap includes a top surface and an annular shoulder depending therefrom having an inner surface, wherein at least a portion of the inner surface of the annular shoulder and the outer surface of the inner tube interact to form a seal.

20. The specimen collection container of claim 19, wherein the seal comprises a tortuous fluid path.

21. The specimen collection container of claim 8, wherein the specimen collection cap includes a top surface and an annular shoulder depending therefrom having an inner surface, wherein at least a portion of the inner surface of the annular shoulder and the outer surface of the outer tube interact to form a seal.

22. The specimen collection container of claim 21, wherein the seal comprises a tortuous fluid path.

* * * * *